United States Patent [19]

Acton et al.

[11] 4,314,054
[45] Feb. 2, 1982

[54] 3'-DEAMINO-3'-(4-METHOXY-1-PIPERIDI-NYL) DERIVATIVES OF DAUNORUBICIN AND DOXORUBICIN

[75] Inventors: Edward M. Acton, Menlo Park; Carol W. Mosher, Stanford, both of Calif.

[73] Assignee: SRI International, Menlo Park, Calif.

[21] Appl. No.: 246,625

[22] Filed: Mar. 23, 1981

[51] Int. Cl.³ .................. A61K 31/70; C07H 15/24
[52] U.S. Cl. ............................. 536/17 A; 424/180
[58] Field of Search .................. 536/17 A; 424/180

[56] References Cited

U.S. PATENT DOCUMENTS

| | | | |
|---|---|---|---|
| 4,035,566 | 7/1977 | Israel et al. | 536/17 A |
| 4,177,264 | 12/1979 | Wu et al. | 536/17 A |
| 4,202,967 | 5/1980 | Tong et al. | 536/17 A |
| 4,250,303 | 2/1981 | Wu et al. | 536/17 A |

OTHER PUBLICATIONS

Henry, Reprint from 'ACS Symposium Series, No. 30, "Cancer Chemotherapy", 1979, pp. 15–57.
Tong et al. "Jour. of Medicinal Chem." vol. 22, No. 8, 1979, pp. 912–918.

*Primary Examiner*—Johnnie R. Brown
*Attorney, Agent, or Firm*—Urban H. Faubion

[57] ABSTRACT

Described are 3'-deamino-3'-(4-methoxy-1-piperidinyl) derivatives of daunorubicin and doxorubicin having the formula

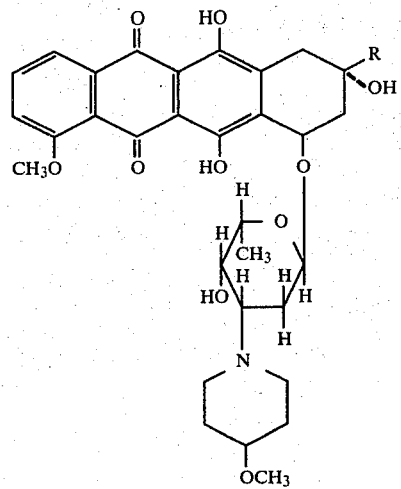

wherein R is $COCH_3$ or $-CHOHCH_3$ in the case of daunorubicin derivatives, or is $COCH_2OH$ or $-CHOH-CH_2OH$ in the case of doxorubicin derivatives together with their pharmaceutically acceptable acid salts. The compounds have utility as antitumor agents.

7 Claims, No Drawings

3'-DEAMINO-3'-(4-METHOXY-1-PIPERIDINYL) DERIVATIVES OF DAUNORUBICIN AND DOXORUBICIN

ORIGIN OF INVENTION

The invention described herein was made in the course of work under a grant (Grant No. CA 25711) from the National Cancer Institute of the Department of Health and Human Services.

BACKGROUND OF INVENTION

Doxorubicin (adriamycin) is perhaps the most useful new anticancer drug in use at this time. It (along with daunorubicin) is a principal agent in the treatment of an unusually wide number of solid tumors and leukemias. Regrettably, many patients with these tumors fail to respond, and essentially no patients with some serious tumor types (colon cancer, melanoma) respond. In addition, chronic treatment produces irreversible heart damage that can be fatal if continued. Thus, there is great need for analogs which give a better rate of response, a wider spectrum of response, or reduced cardiotoxicity. More effective and less toxic agents are widely sought. The most active new analogs so far, judging from screening results in a widely used test against mouse leukemia P388 in a 3-dose treatment schedule (q4d 5,9,13), are two lipophilic derivatives (AD32 and N,N-dibenzldaunorubicin) that required significantly higher doses, and which fail to interact with DNA in vitro although DNA is believed to be a primary biological target for the anthracycline series. Reductive alkylation of doxorubicin and daunorubicin, using an aldehyde or ketone plus $NaBH_3CH$, has proven to be a useful chemical method for modifying the structures to give semisynthetic analogs. Most N-alkyl derivatives have been active in the antitumor screen against mouse leukemia P388, but are not significantly different from doxorubicin or daunorubicin. A few such derivatives have been inactive.

PRIOR ART

Much of the history and prior art of adriamycin and its anthracycline analogs is found in the article "Adriamycin" by David W. Henry, ACS Symposium Series, No. 30, Cancer Chemotherapby, American Chemical Society, pp. 15-57, (1976). For example, AD32 is disclosed and discussed there and also in U.S. Pat. No. 4,035,566, dated July 12, 1977.

N,N-Dibenzyldaunorubicin is disclosed in U.S. Pat. Nos. 4,177,264 and 4,250,303, respectively, dated Dec. 4, 1979 and Feb. 10, 1981, both issued to Helen Y. Wu, Thomas H. Smith and David W. Henry and assigned to the assignee of the present invention.

3'-Deamino-3'-(1-piperidinyl)daunorubicin (synonym for N,N-pentamethylenedaunorubicin) (found in U.S. Pat. No. 4,202,967, which issued May 13, 1980, to Tong, Henry, Wu and Smith and also assigned to the assignee of the present invention), showed improved activity over doxorubicin, but not to an exceptional degree (survival time of treated animals/controls=T/C=177% vs 160% against mouse leukemia P388, q4d 5,9,13.

3'-Deamino-3'-(4-morpholinyl)daunorubicin, disclosed in copending application Ser. No. 199,082, filed Oct. 20, 1980, in the name of the present inventors and assigned to the assignee of the present application, was active at one-fortieth the dose of doxorubicin but gave a substantially identical T/C value (166% vs 160% against P388).

The general reductive alkylation process for preparing new semi-synthetic anthracycline derivatives is described in "Adriamycin Analogs. 3. Synthesis of N-Alkylated Anthracyclines With Enhanced Efficacy and Reduced Cardiotoxicity", J. Medicinal Chem., 22, No. 8, pp 912–918, (1979) by G. L. Tong. H. Y. Wu, T. H. Smith and D. W. Henry. The subject matter of this article and the above cited prior art is specifically incorporated herein by reference.

SUMMARY OF INVENTION

The present invention relates to the provision of novel daunorubicin and doxorubicin derivatives having the formula 1 to 4,

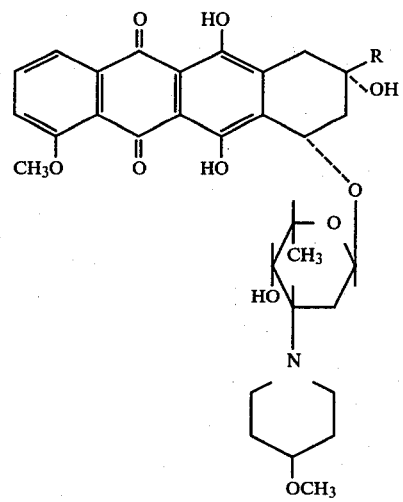

1, R = $COCH_3$
2, R = $CHOH-CH_3$
3, R = $CO-CH_2OH$
4, R = $CHOH-CH_2OH$ where R is $COCH_3$ or $-CHOHCH_3$ in the case of daunorubicin derivatives, or is $COCH_2OH$ or $CHOH-CH_2OH$ in the case of doxorubicin derivatives. Specifically, the invention covers the compounds 3'-deamino-3'-(4-methoxy-1-piperidinyl) daunorubicin (1); 3'-deamino-3'-(4-methoxy-1-piperidinyl)-13-dihydrodaunorubicin (2); 3'-deamino-3'-(4-methoxy-1-piperidinyl)doxorubicin (3); and 3'-deamino-3'-(4-methoxy-1-piperidinyl)-13-dihydrodoxorubicin (4), together with their pharmaceutically acceptable acid addition salts.

These new compounds are related to the established anticancer drugs daunorubicin and doxorubicin, and are prepared from them by chemical synthetic methods, using 3-methoxyglutaraldehyde and sodium cyanoborohydride in a reductive alkylation procedure, as set forth in the examples below. The new compounds of this invention have proven to be distinctly active against cancer when tested against model tumors in mice. In particular, they appear superior to doxorubicin in extending the survival time of the tumor-bearing mice.

The compounds of the present invention can be prepared either in the free base or acid addition salt form. The salts are soluble in water and aqueous propylene glycol, for example, while the compounds in free base form are soluble in selected organic solvents such as chloroform, methylene chloride and ethyl acetate.

The salts are particularly well adapted for use in antitumor applications since they may be used in aqueous (including saline) solution form. Good choices for these acid addition salts (prepared in a preferred embodiment as those of HCl) are the pharmaceutically acceptable, nontoxic addition salts with suitable inorganic acids such as hydrochloric, hydrobromic, nitric, sulphuric and phosphoric acids. Other suitable acid candidates for the acid addition salt combination are acids, such as organic carboxylic acids (e.g., glycolic, maleic, hydroxymaleic, malic, tartaric, citric, salicylic) and organic sulphonic acids (e.g., methanesulphonic and p-toluenesulfonic).

With respect to the free base used in the preparation of compounds of the present invention, an acid addition salt can be converted into the free compound by any of a number of well known methods. For example, the acid addition salt can be treated with a base, a metal carbonate, hydrogen carbonate, ammonia, a hydroxyl ion exchange resin or any other suitable reagent. Considering the base, almost any metal hydroxide or alkoxide will do; by way of example, alkali metal hydroxides or alkaline earth metal hydroxides such as lithium hydroxide, sodium hydroxide, potassium hydroxide or calcium hydroxide may be used. Carbonates of the alkali metals or alkaline earth metals which can be used include the carbonates of sodium, potassium or calcium.

Acid addition salts used in preparing compounds of the present invention may also be derived by converting one acid addition salt into the acid addition salt to be used, by any one of a number of well known methods. For example, it is known that such a conversion can be made using a salt of the compound with an inorganic acid and treating the combination with a metal salt. That is, the kind of reaction where a suitable diluent contains an acid salt of, for example, sodium, barium, or silver, and this diluent (including the acid salt) is used to treat a salt of the compound with an inorganic acid; an insoluble inorganic salt is then formed and is removed from the reaction medium. An acid addition salt may also be converted into another acid addition salt by treatment with an anion exchange preparation.

The preparation of the compounds of the present invention is illustrated in the following example:

EXAMPLE

3'-Deamino-3'-(4-methoxy-1-piperidinyl)daunorubicin (1) and 3'-deamino-3'-(4-methoxy-1-piperidinyl)-13-dihydrodaunorubicin (2)

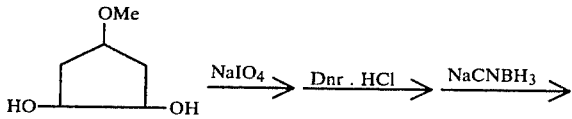

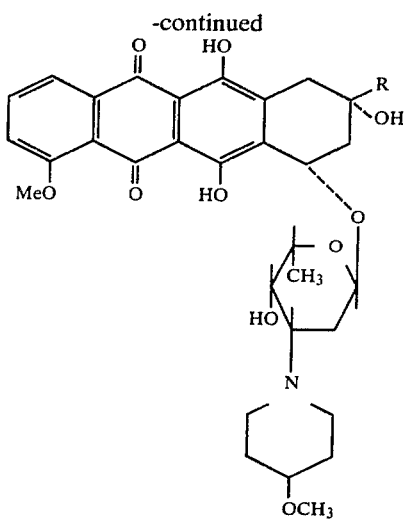

1 R = C(O)CH$_3$
2 R = CHOH—CH$_3$

To a solution of 1,2-dihydroxy-4-methoxycyclopentane (408 mg, 3.08 mmoles) in 5 ml of H$_2$O, was added, with stirring NaIO$_4$ (660 mg, 3.08 mmoles) in several portions. More H$_2$O, 4 ml, was added to dissolve solid that separated after a few minutes. After the solution had stood for 3 hours at room temperature, acetonitrile, 30 ml, was added, followed by daunorubicin hydrochloride (1.128 g, 2 mmoles). The red solution was stirred for 45 minutes and then a solution of NaCNBH$_3$ (248 mg, 4 mmoles) in 10 ml acetonitrile was added. Stirring at room temperature was continued for 2 hours. After the reaction mixture had been diluted with 40 ml of H$_2$O is was extracted thoroughly with several portions of chloroform. The washed and dried extracts were concentrated, leaving 1.47 g of solid residue. Purification was effected by flash chromatography on silica gel 60 (230-400 mesh) and by thick layer chromatography, using CHCl$_3$-methanol (8:1), to yield 294 mg of 1 and 146 mg of 2.

Each of these products was separately converted to the corresponding hydrochloride by mixing the amorphous solid with water and then dilute HCl until solution was complete, when the pH was 4. In each case, the clear red solution was lyophilized to yield a fluffy red solid that was triturated with ether, collected on a filter and dried in vacuo. Weight of 1.HCl was 232 mg, Rf 0.20 by TLC on silica gel in CHCl$_3$-methanol (8:1), of 2.HCl was 121 mg, Rf 0.09 by TLC.

By a practice of the methods described in the foregoing example, but with the use of doxorubicin hydrochloride rather than daunorubicin hydrochloride, there may be prepared corresponding doxorubicin derivatives such as 3'-deamino-3'-(4-methoxy-1-piperidinyl) doxorubicin hydrobromide and 3'-deamino-3'-(4-methoxy-1-piperidinyl-13-dihydrodoxorubicin hydrochloride.

As indicated above, the compounds of the present invention have improved antitumor activity. This is evidenced by the data given below. In one operation, conducted in accordance with the protocol described in Cancer Chemotherapy Reports, National Cancer Institute, Vol. 3, No. 2, Part 3, September 1972, healthy mice were inoculated i.p. with Lymphocytic Leukemia P-388 ascitic fluid. The inoculated mice were then treated on days 5, 9 and 13 of the succeeding period with various amounts of chemicals 1 and 2 described in the example given above while other of the mice were similarly inoculated, for comparison purposes, with daunorubicin, doxorubicin, the N,N-pentamethylenedaunorubicin hydrochloride compound of U.S. Pat. No. 4,202,967 or the 3'-deamino-3'-(4-morpholinyl) daunorubicin hydrobromide compound of Edward M. Acton and Carol W. Mosher's application filed Oct. 20, 1980, as Ser. No. 199,082. The average survival time of the treated mice was then determined as was that of the control mice which had been inoculated with the leukemia ascitic fluid but given no treatment with the test chemicals. Presented in the following table under the percent T/C column heading are the data so obtained. T/C values are determined by dividing the survival time of the treated mice by that of the control mice, the quotient so obtained being multiplied by 100.

Also presented in the table are the optimum dosage levels of the test chemicals (in terms of mg per kg of body weight) which produce the best antitumor response.

| | | BIOLOGICAL TEST DATA | |
|---|---|---|---|
| | | Activity vs Leukemia P388 in Mice | |
| Compound | NSC No. | Survival time Treated mice/ Control mice % TC | Optimum dose q4d 5,9,13 mg/kg |
| HCl salt 1 | 334353 | 199 | 6.25 |
| 13-Dihydro HCl salt 2 | 334354 | 199 | 12.5 |
| For comparison: | | | |
| Doxorubicin . HCl | 123127 | 160 | 8.0 |
| Daunorubicin . HCl | 82151 | 130 | 8.0 |
| N,N-Pentamethylene-daunorubicin . HCl | 329687 | 177 | 6.25 |
| 3'-Deamino-3'-(4-morpholinyl)-daunorubicin . HBr | 327451 | 166 | 0.20 |

It will be observed that the activity of 1 and 2 is significantly improved over that of doxorubicin as measured by the survival time of the test animals (i.e., T/C=199% compared with 160%). At the same time there was no signficant change in the dose level required. The survival time after treatment with 1 and 2 was also improved over that after treatment with the related analogs, N,N-pentamethylenedaunorubicin hydrochloride (T/C=177%) and 3'-deamino-3'-(4-morpholinyl) daunorubicin (T/C=166%). The latter was distinctive in requiring a much lower dose (one-fortieth that of doxorubicin), but 1 and 2 are distinctive in providing significantly improved survival time at the same dose level as that of doxorubicin. Previously, among the several hundred doxorubicin analogs reported, higher T/C values (209%) in this test system apparently were observed only with two lipophilic analogs (N,N-dibenzyldaunorubicin and AD32, cited under Prior Art) that required much higher doses.

What is claimed is:

1. Compounds of the formula

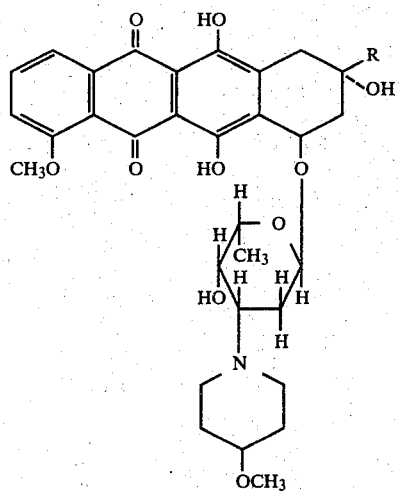

wherein R is selected from the group consisting of —COCH$_3$, —CHOHCH$_3$, —COCH$_2$OH and —CHOHCH$_2$OH and the pharmaceutically acceptable acid addition salts of said compounds.

2. The compound of claim 1 which is 3'-deamino-3'-(4-methoxy-1-piperidinyl)daunorubicin and its pharmaceutically acceptable acid addition salts.

3. The compound of claim 2 which is 3'-deamino-3'-(4-methoxy-1-piperidinyl)daunorubicin hydrochloride.

4. The compound of claim 1 which is 3'-deamino-3'-(4-methoxy-1-piperidinyl)-13-dihydrodaunorubicin and its pharmaceutically acceptable salt.

5. The compound of claim 4 which is 3'-deamino-3'-(4-methoxy-1-piperidinyl)-13-dihydrodoxorubicin hydrochloride.

6. The compound of claim 1 which is 3'-deamino-3'-(4-methoxy-1-piperidinyl)doxorubicin and its pharmaceutically acceptable acid addition salts.

7. The compound of claim 1 which is 3'-deamino-3'-(4-methoxy-1-piperidinyl)-13-dihydrodoxorubicin and its pharmaceutically acceptable acid addition salts.

* * * * *